United States Patent
Saito et al.

(10) Patent No.: US 10,506,932 B2
(45) Date of Patent: Dec. 17, 2019

(54) VASCULAR VISCOELASTICITY EVALUATION DEVICE, VASCULAR VISCOELASTICITY EVALUATION METHOD, AND PROGRAM

(71) Applicants: SHISEI DATUM CO., LTD., Machida-shi, Tokyo (JP); RIKEN, Hirosawa, Wako-shi, Saitama (JP)

(72) Inventors: Yukiyoshi Saito, Machida (JP); Ryutaro Himeno, Wako (JP); Shu Takagi, Wako (JP); Fuyou Liang, Wako (JP)

(73) Assignees: Shisei Datum Co., Ltd., Tokyo (JP); RIKEN, Saitama (JP)

(*) Notice: Subject to any disclaimer, the term of this patent is extended or adjusted under 35 U.S.C. 154(b) by 1088 days.

(21) Appl. No.: 14/780,259

(22) PCT Filed: Mar. 24, 2014

(86) PCT No.: PCT/JP2014/059385
§ 371 (c)(1),
(2) Date: Sep. 25, 2015

(87) PCT Pub. No.: WO2014/157714
PCT Pub. Date: Oct. 2, 2014

(65) Prior Publication Data
US 2016/0051151 A1    Feb. 25, 2016

(30) Foreign Application Priority Data
Mar. 26, 2013 (JP) .................. 2013-063787

(51) Int. Cl.
*A61B 5/02* (2006.01)
*A61B 5/021* (2006.01)
(Continued)

(52) U.S. Cl.
CPC .......... *A61B 5/02007* (2013.01); *A61B 5/022* (2013.01); *A61B 5/02116* (2013.01); *A61B 5/7271* (2013.01)

(58) Field of Classification Search
CPC ..... A61B 5/022; A61B 5/7271; A61B 5/7239; A61B 5/02
See application file for complete search history.

(56) References Cited

U.S. PATENT DOCUMENTS

2009/0306523 A1* 12/2009 Saito ...................... A61B 5/02
600/481

FOREIGN PATENT DOCUMENTS

| JP | 2000-51166 A | 2/2000 |
|----|---|---|
| JP | 2002-238867 A | 8/2002 |

(Continued)

OTHER PUBLICATIONS

Cong Luo et al. "Measurement and Clinical Study of Arterial Compliance", Automation Congress, 2008, WAC 2008, World, IEEE, Piscataway, NJ, USA, Sep. 28, 2008 (Sep. 28, 2008), pp. 1-4.
(Continued)

*Primary Examiner* — Christian Jang
(74) *Attorney, Agent, or Firm* — DLA Piper LLP (US)

(57) ABSTRACT

A vascular viscoelasticity evaluation device and method in which, a pulse wave obtained using a cuff is subjected to first derivation, a positive amplitude peak value Vf1 that occurs first and a negative amplitude peak value Vr2 that occurs second out of a plurality of negative amplitude peak values are detected in a state in which an external force substantially the same as or greater than the systolic blood pressure has been exerted on a blood vessel, and a ratio of the positive amplitude peak value Vf1 that occurs first to the negative
(Continued)

amplitude peak value Vr2 that occurs second is calculated, and then the vascular viscoelasticity is evaluated on the basis of this calculated ratio.

13 Claims, 15 Drawing Sheets

(51) Int. Cl.
  *A61B 5/022* (2006.01)
  *A61B 5/00* (2006.01)

(56) References Cited

FOREIGN PATENT DOCUMENTS

| | | |
|---|---|---|
| JP | 4054884 B1 | 3/2008 |
| JP | 2008-161644 A | 7/2008 |
| JP | 2011-72674 A | 4/2011 |
| WO | 2010058484 A1 | 5/2010 |

OTHER PUBLICATIONS

International Search Report dated May 27, 2014 (May 27, 2014) for a counterpart PCT Application No. PCT/JP2014/59385.
Extended European Search Report dated Jan. 23, 2017 (Jan. 23, 2017), issued in corresponding European Patent Application No. EP 14774331.4 (EP 14 77 4331).

\* cited by examiner

20: CPU

Cuff pressure during blood pressure measurement by oscillometric method

Differential pulse waveform during one pulse

Differential pulse waveform from young person or healthy adult

Differential pulse waveform from elderly person or patient with arterial sclerosis 20a: CPU Ratio Vr1/Vf1 and RT characteristics regarding age Ratio Vr1/Vf1 and RT characteristics regarding hardness of brachial blood vessel (age 25)

Ratio Vr1/Vf1 and RT characteristics regarding hardness of brachial blood vessel (age 55)

Ratio Vr1/Vf1 and RT characteristics regarding hardness of brachial blood vessel (age 85)

300: Vascular viscoelasticity evaluation device

VASCULAR VISCOELASTICITY EVALUATION DEVICE, VASCULAR VISCOELASTICITY EVALUATION METHOD, AND PROGRAM

TECHNICAL FIELD

The present invention relates to a device, method, and program for non-invasively evaluating the degree of vascular viscoelasticity by analyzing pulse waves.

BACKGROUND ART

Pulse wave propagation velocity (PWV) has been a widespread device for evaluating vascular viscoelasticity non-invasively up to now. In this method, pulse waves must be measured using a cuff or the like attached at two or more places.

Meanwhile, there are known devices for evaluating vascular viscoelasticity by pulse wave measurement with a cuff attached at only one place, in which the pulse wave component of the cuff pressure is extracted, this extracted pulse wave component is subjected to temporal differentiation to calculate first derivation value and form a differential waveform, and in a state in which an external force substantially the same as or greater than the systolic blood pressure is being exerted on the blood vessel, the positive amplitude peak value within one pulse wave of the differential waveform is detected, the negative amplitude peak value is detected in a pulse wave in which the positive amplitude peak value was detected, the ratio of the peak value of the positive amplitude to the peak value of the negative amplitude is calculated, and then the vascular viscoelasticity is evaluated on the basis of this calculated ratio (see Patent Reference 1, for example).

PRIOR-ART DOCUMENT

Patent Reference

Patent Reference 1: Japanese Patent No. 4,054,884

SUMMARY OF THE INVENTION

Problems to be Solved by the Invention

Within one pulse wave of the differentiated waveform of a relatively young person, of the negative amplitude peaks, the first peak value that occurs is usually the maximum peak value. When pulse waves are measured for this relatively young person using the device disclosed in Patent Reference 1, since the above-described maximum peak value is used as data for evaluating vascular viscoelasticity, a problem is that reliability of the evaluation of the vascular viscoelasticity is low.

It is an object of the present invention to provide a vascular viscoelasticity evaluation device, a vascular viscoelasticity evaluation method, and a program with which vascular viscoelasticity can be evaluated with high reliability when a pulse wave is measured with a single cuff, and a determination index for vascular viscoelasticity is calculated on the basis of this measured pulse wave, and when calculating the determination index for vascular viscoelasticity wherein the measurement subject is a relatively young person.

The viscoelasticity of a blood vessel has been shown to be associated with atherosclerosis, and the risk of arteriosclerosis rises in proportion to the hardness of a blood vessel. In particular, the viscoelasticity of the blood vessels of a central artery is held to have great clinical significance, and being able to accurately evaluate the viscoelasticity of a central artery with a single cuff has considerable importance from a societal perspective.

Means for Solving the Problems

Within one pulse wave of a differential waveform obtained by temporal differentiation of a pulse wave component extracted in a state that an external force that is substantially the same as or greater than the systolic blood pressure has been exerted on a blood vessel, a positive amplitude peak value Vf1 that occurs first and a peak Vr2 that occurs second out of a plurality of negative amplitude peak values are detected, a ratio of the positive amplitude peak value Vf1 that occurs first with respect to the negative amplitude peak value Vr2 that occurs second is calculated, and vascular viscoelasticity is evaluated on the basis of this calculated ratio.

Effects of the Invention

According to the present invention such an effect is provided that vascular viscoelasticity can be evaluated with high reliability when a pulse wave is measured with a single cuff, and a determination index for vascular viscoelasticity is calculated on the basis of this measured pulse wave, and when the determination index for vascular viscoelasticity is calculated with the measurement subject being a relatively young person.

Also, since the evaluation is made on the basis of the above-described calculated ratio, the viscoelasticity of a central artery can be accurately evaluated without being affected by the hardness of brachial blood vessels.

MODES FOR CARRYING OUT THE INVENTION

Embodiments of the invention are presented below by the following embodiments.

Embodiment 1

Figure 1:
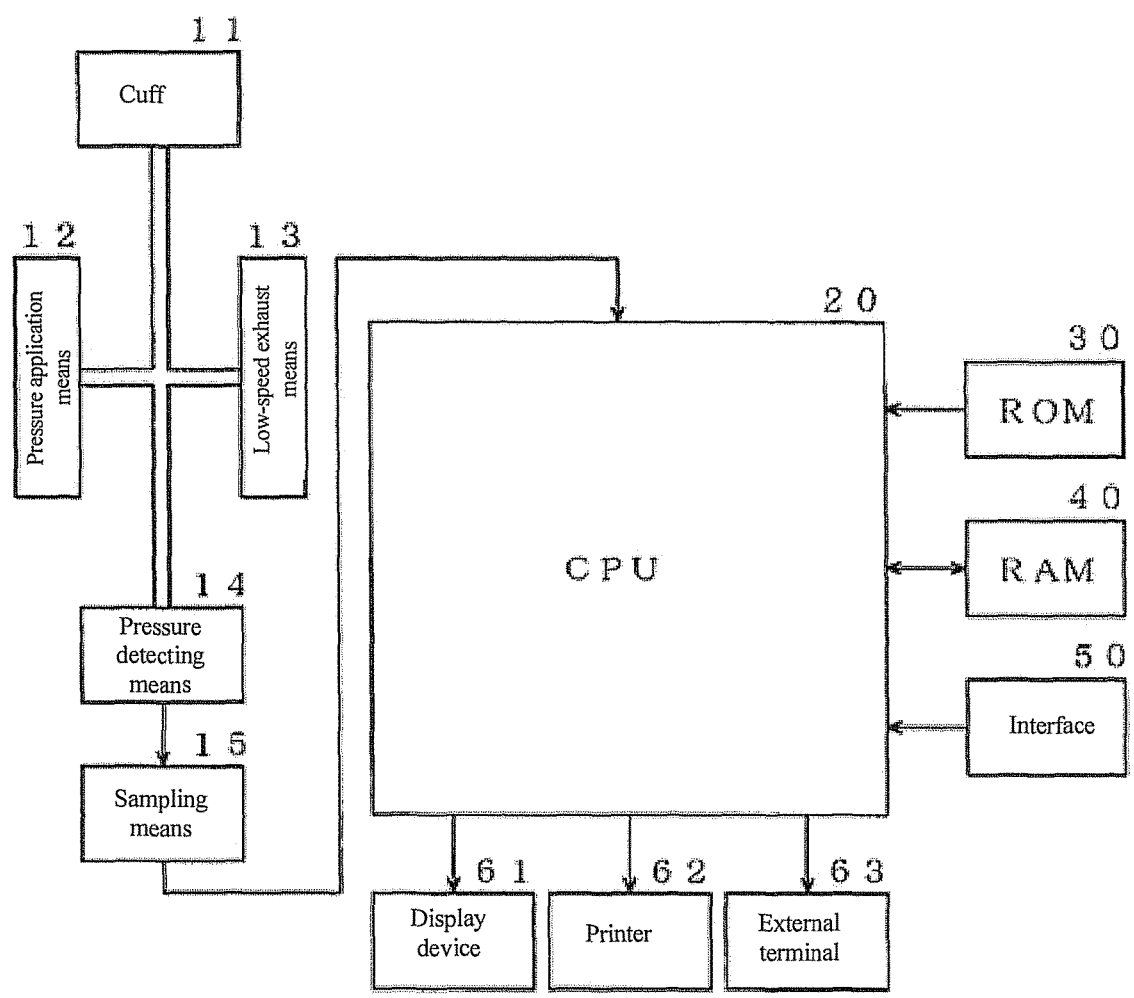
FIG. 1 is a block diagram of a vascular viscoelasticity evaluation device 100 according to Embodiment 1 of the present invention.

FIG. 1 is a block diagram of a vascular viscoelasticity evaluation device 100 of Embodiment 1 of the present invention.

The vascular viscoelasticity evaluation device 100 is comprised of a cuff 11, a pressure application means 12, a low-speed exhaust means 13, a pressure detecting means 14, a sampling means 15, a CPU 20, a ROM 30, a RAM 40, an interface 50, a display device 61, a printer 62, and an external terminal 63.

The cuff 11, the pressure application means 12, the low-speed exhaust means 13, and the pressure detecting means 14 are connected by flexible tubing. Also, the pressure application means 12, the low-speed exhaust means 13, the pressure detecting means 14, and the sampling means 15 are controlled by the CPU 20.

The cuff 11 is wrapped around the arm, wrist, finger, thigh, ankle, etc., of a measurement subject to obtain a pulse wave. The pressure application means 12 pressurizes the cuff 11 to a predetermined pressure needed for blood pressure measurement. The low-speed exhaust means 13 gradually releases the pressure inside the cuff 11 pressurized by the pressure application means 12.

The pressure detecting means 14 includes a pressure transducer for detecting the pressure of the cuff 11, and it converts the above-described pressure into an electrical signal (pulse) and outputs the result. The sampling means 15 counts the number of electrical signals (pulses) from the pressure detecting means 14 within a specific length of time, and it repeats this count periodically in response to a sampling signal, and further subjects the sampled value to A/D conversion.

Figure 2:
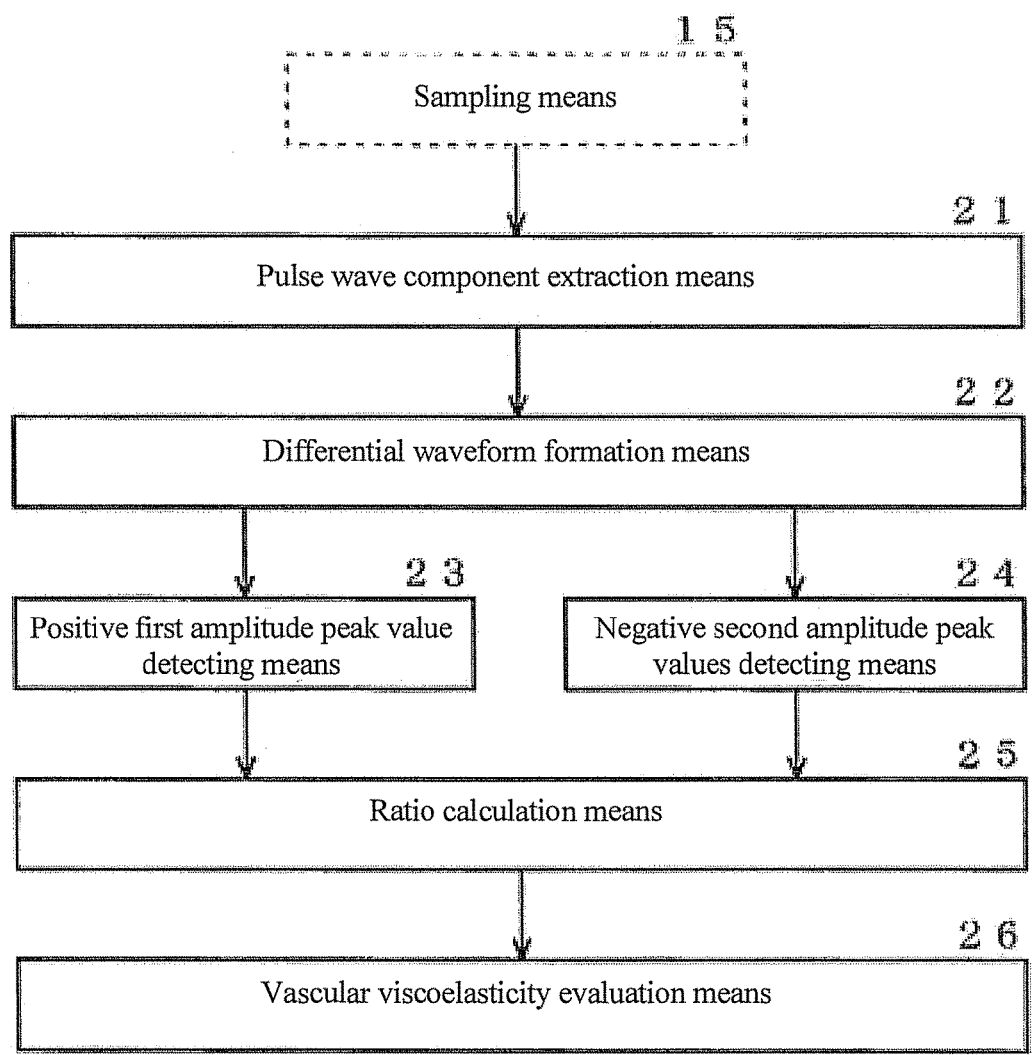
FIG. 2 is a block diagram illustrating the functions of a CPU 20.

FIG. 2 is a block diagram illustrating the function of the CPU 20.

Figure 9:
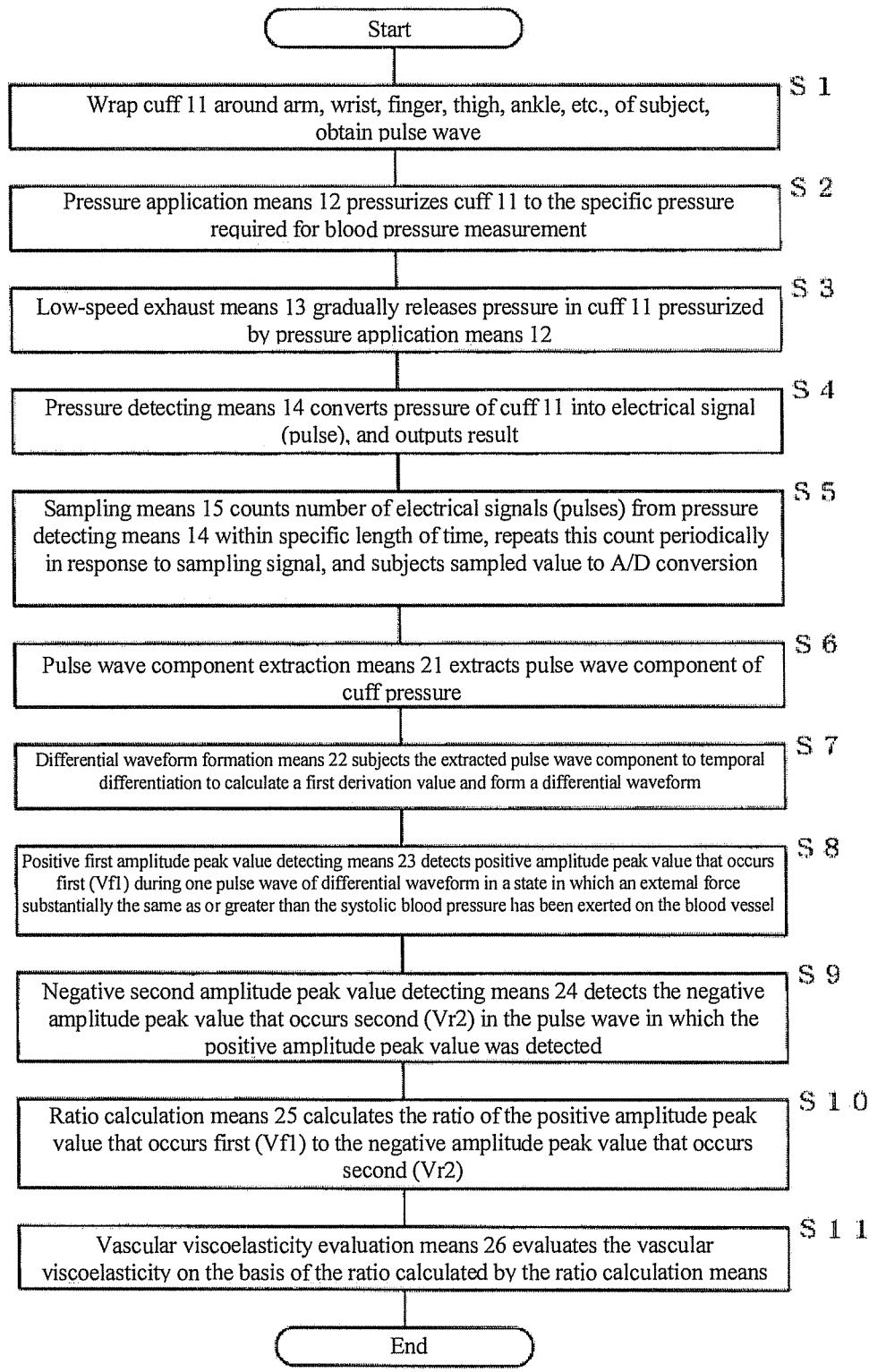
FIG. 9 is a flowchart of the operation in Embodiment 1.

The CPU 20 controls the entire vascular viscoelasticity evaluation device 100, and functionally, it works in conjunction with programs stored in the ROM 30 (a corresponding flowchart is shown in FIG. 9) to form implementation of a pulse wave component extraction means 21, a differential waveform formation means 22, a positive first amplitude peak value detecting means 23, a negative second amplitude peak value detecting means 24, a ratio calculation means 25, and a vascular viscoelasticity evaluation means 26.

The pulse wave component extraction means 21 extracts the pulse wave component of the cuff pressure. The differential waveform formation means 22 subjects the pulse wave component extracted by the pulse wave component extraction means 21 to temporal differentiation to calculate a first derivation value and form a differential waveform.

In a state in which an external force substantially the same as the systolic blood pressure has been exerted on a blood vessel, the positive first amplitude peak value detecting means 23 detects the positive amplitude peak value Vf1 that occurs first within one pulse wave of the above-described differential waveform.

The negative second amplitude peak value detecting means 24 detects the negative amplitude peak value Vr2 that occurs second in the pulse wave in which the positive amplitude peak value Vf1 that occurs first was detected. The ratio calculation means 25 calculates the ratio RT (Vr2/Vf1) of the positive amplitude peak value Vf1 that occurs first with respect to the negative amplitude peak value Vr2 that occurs second. The vascular viscoelasticity evaluation means 26 evaluates vascular viscoelasticity on the basis of the ratio RT calculated by the ratio calculation means 25.

Figure 3:
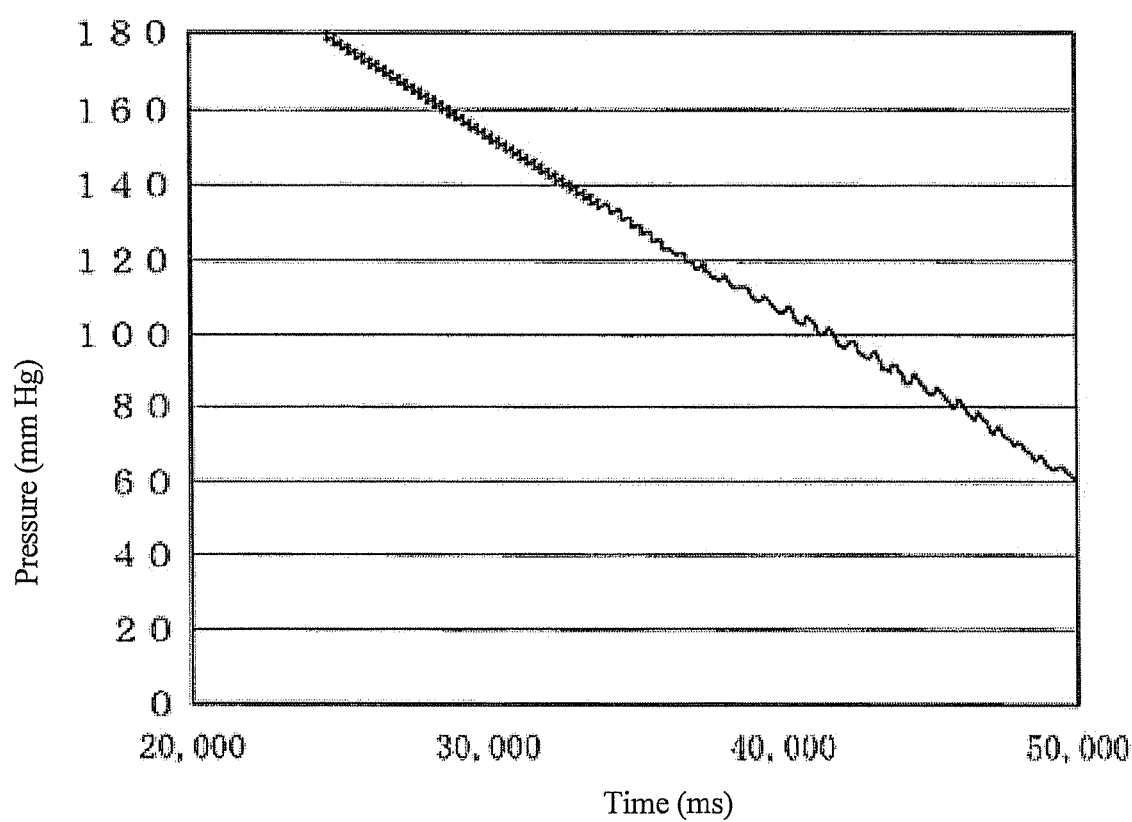
FIG. 3 is a graph of changes in cuff pressure in Embodiment 1.

FIG. 3 is a graph illustrating the changes in cuff pressure in Embodiment 1.

The cuff 11 is wrapped around an arm, wrist, finger, etc. The pressure inside this cuff 11 is raised to a specific level by the pressure application means 12, after which it is reduced substantially linearly by the low-speed exhaust means 13 at a rate of 3 to 5 mm Hg/second. The pulse wave amplitude component is superposed over the cuff pressure during the course of this depressurization.

How the vascular viscoelasticity evaluation device 100 computes an index for vascular viscoelasticity will now be described more concretely. First, the cuff 11 is wrapped around the arm of a measurement subject, a measurement start switch provided to the interface 50 is turned on, which pressurizes the cuff 11 with the pressure application means 12 until the pressure required for blood pressure measurement is reached, then the pressure application is halted, and the low-speed exhaust means 13 next gradually exhausts the air inside the cuff 11, so that the pressure displacement brought about by the pulse wave component thereby begins to be transmitted to the cuff.

The pressure detecting means 14 converts the cuff pressure into an electrical signal as a change in frequency, and the sampling means 15 samples at regular time intervals (for example, every 5 ms) and outputs a pulse in response to the sampled cuff pressure.

Figure 4:
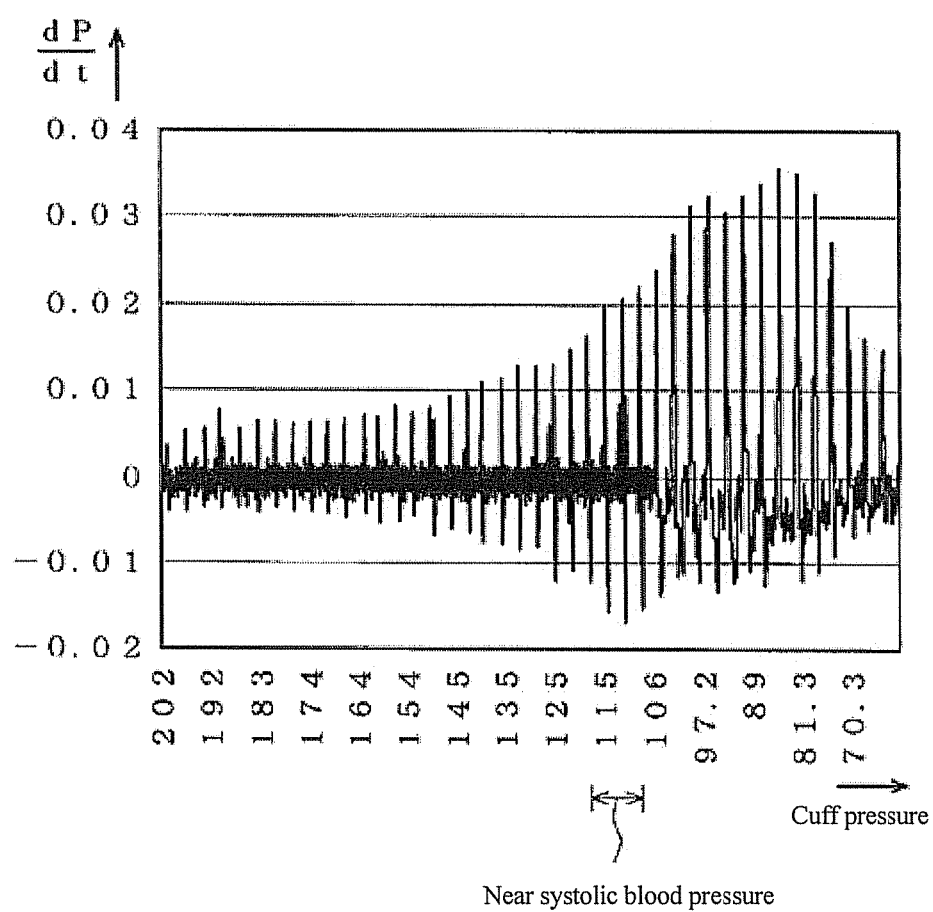
FIG. 4 is a detailed view of a relation (dP/dt) between the change in cuff pressure and the amplitude value.

FIG. 4 is a detailed view of the relation between the cuff pressure change and the amplitude value (dP/dt).

Figure 5:
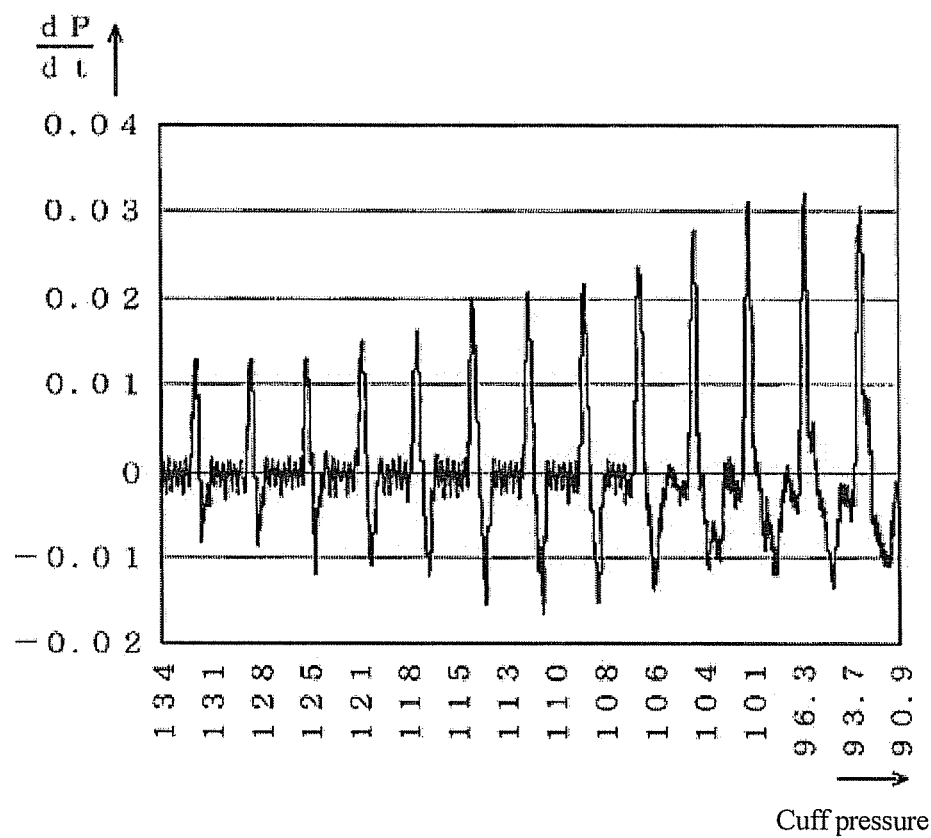
FIG. 5 is a detailed view of a differential pulse wave near the systolic blood pressure in Embodiment 1.
Figure 5:
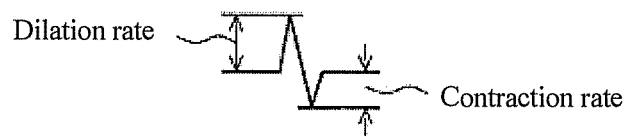

FIG. 5 is a detailed view of a differential pulse wave near the systolic blood pressure in Embodiment 1.

When temporal differentiation is made for cuff pressure and the depressurization rate is removed from the cuff pressure, then a differential pulse wave can be obtained as shown in FIG. 4. In FIG. 4, the positive amplitude peak value Vf1 that occurs first is the value of the peak out of the differential waveform within one pulse wave and out of the amplitude values in the positive direction relative to zero. Also, in FIG. 4, the negative amplitude peak value Vr2 that occurs second is the value of the peak that occurs second out of this differential waveform within one pulse wave and out of the amplitude values in the negative direction relative to zero.

A temporal differential pulse wave is a value indicative of the rate at which the volume of a blood vessel changes. A positive amplitude value indicates the dilation rate of the blood vessel, and a negative amplitude value indicates the contraction rate of the blood vessel.

Figure 6:
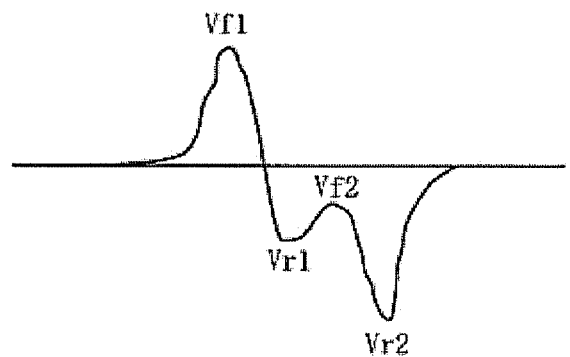
FIG. 6 is a detailed view of one pulse of a differential pulse waveform.

FIG. 6 is a detailed view of one pulse of a differential pulse waveform.

The detailed view of the one-pulse differential waveform of FIG. 6 is a further enlargement of FIG. 5, focusing on the temporal differential pulse wave within one pulse. The differential pulse wave within one pulse includes the positive amplitude peak value Vf1 that occurs first, the positive amplitude peak value Vf2 that occurs second, the negative amplitude peak value Vr1 that occurs first, and the negative amplitude peak value Vr2 that occurs second.

Figure 7:
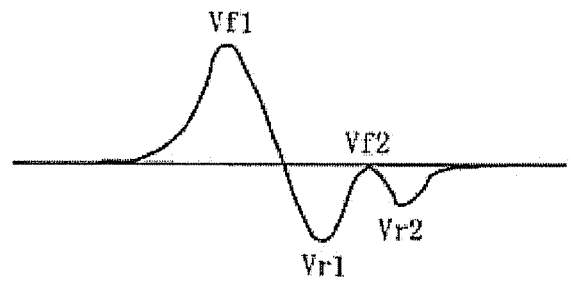
FIG. 7 shows one pulse of a differential pulse waveform from a young person.

FIG. 7 shows one pulse of a differential pulse waveform from a young person.

Figure 8:
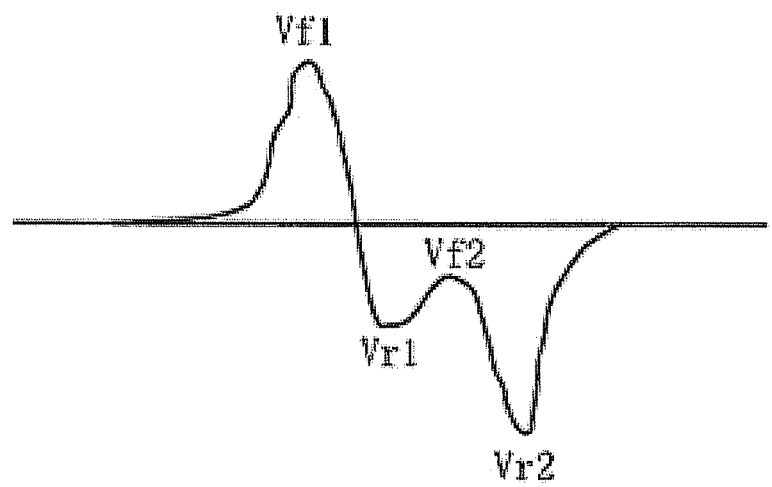
FIG. 8 shows a differential pulse waveform from an elderly person and a patient with arterial sclerosis.

FIG. 8 shows a differential pulse waveform from an elderly person and a patient with arterial sclerosis.

As is clear from FIGS. 7 and 8, the negative amplitude peak value Vr2 that occurs second is relatively greater than the other peak values, depending on age and vascular viscoelasticity. Therefore, vascular viscoelasticity can be evaluated on the basis of the ratio RT of the positive amplitude peak value Vf1 that occurs first to the negative amplitude peak value Vr2 that occurs second. In other words, vascular viscoelasticity can be properly evaluated by using the ratio RT between the positive amplitude peak value Vf1 that occurs first and the negative amplitude peak value Vr2 that occurs second.

Next, the operation in Embodiment 1 will be described.

FIG. 9 is a flowchart of the operation in Embodiment 1.

First, in S1, the cuff 11 is wrapped around the arm, wrist, finger, thigh, ankle, etc., of a measurement subject to obtain a pulse wave. In S2, the specific pressure required for blood pressure measurement is applied to the cuff 11 via the pressure application means 12. In S3, the pressure inside the cuff 11 applied by the pressure application means 12 is gradually released by the low-speed exhaust means 13.

In S4, the pressure detecting means 14 converts the pressure of the cuff 11 into an electrical signal (pulse) and outputs the result. In S5, the sampling means 15 counts the number of electrical signals (pulses) from the pressure detecting means 14 within a specific length of time, repeats this count periodically in response to a sampling signal, and subjects the sampled value to A/D conversion.

In S6, the pulse wave component extraction means 21 extracts the pulse wave component of the cuff pressure. In S7, the differential waveform formation means 22 subjects the extracted pulse wave component to temporal differentiation to calculate a first derivation value and form a differential waveform.

In S8, the positive first amplitude peak value detecting means 23 detects the positive amplitude peak value Vf1 that occurs first within one pulse wave of the differential waveform in a state that an external force substantially the same as or greater than the systolic blood pressure has been exerted on a blood vessel. In S9, the negative second amplitude peak value detecting means 24 detects the negative amplitude peak value Vr2 that occurs second in the pulse wave in which the positive amplitude peak value Vf1 that occurs first has been detected.

In S10, the ratio calculation means 25 calculates the ratio RT of the positive amplitude peak value Vf1 that occurs first with reference to the negative amplitude peak value Vr2 that occurs second. In S11, the vascular viscoelasticity evaluation means 26 evaluates vascular viscoelasticity on the basis of the ratio RT calculated by the ratio calculation means 25.

In Embodiment 1, reliability in the evaluation of vascular viscoelasticity is high when a pulse wave is measured with a single cuff and a determination index for vascular viscoelasticity is calculated on the basis of this measured pulse wave, and when the determination index for vascular viscoelasticity is calculated for a measurement subject that is a relatively young person.

More specifically, when the hardness of a central artery in a human body is simulated on a computer and the parameters for hardening the central artery are controlled, this is reflected in the negative amplitude peak value Vr2 that occurs second. Therefore, by way of calculating the ratio RT of the positive amplitude peak value Vf1 that occurs first to the negative amplitude peak value Vr2 that occurs second and then evaluating vascular viscoelasticity on the basis of the ratio RT, it is possible to improve the reliability in the evaluation of vascular viscoelasticity for relatively young subjects.

Also, in the above embodiment, a difference can be used instead of using a ratio. In other words, the vascular viscoelasticity can be evaluated on the basis of the difference between the positive amplitude peak value Vf1 that occurs first and the negative amplitude peak value Vr2 that occurs second.

Embodiment 2

Figure 10:
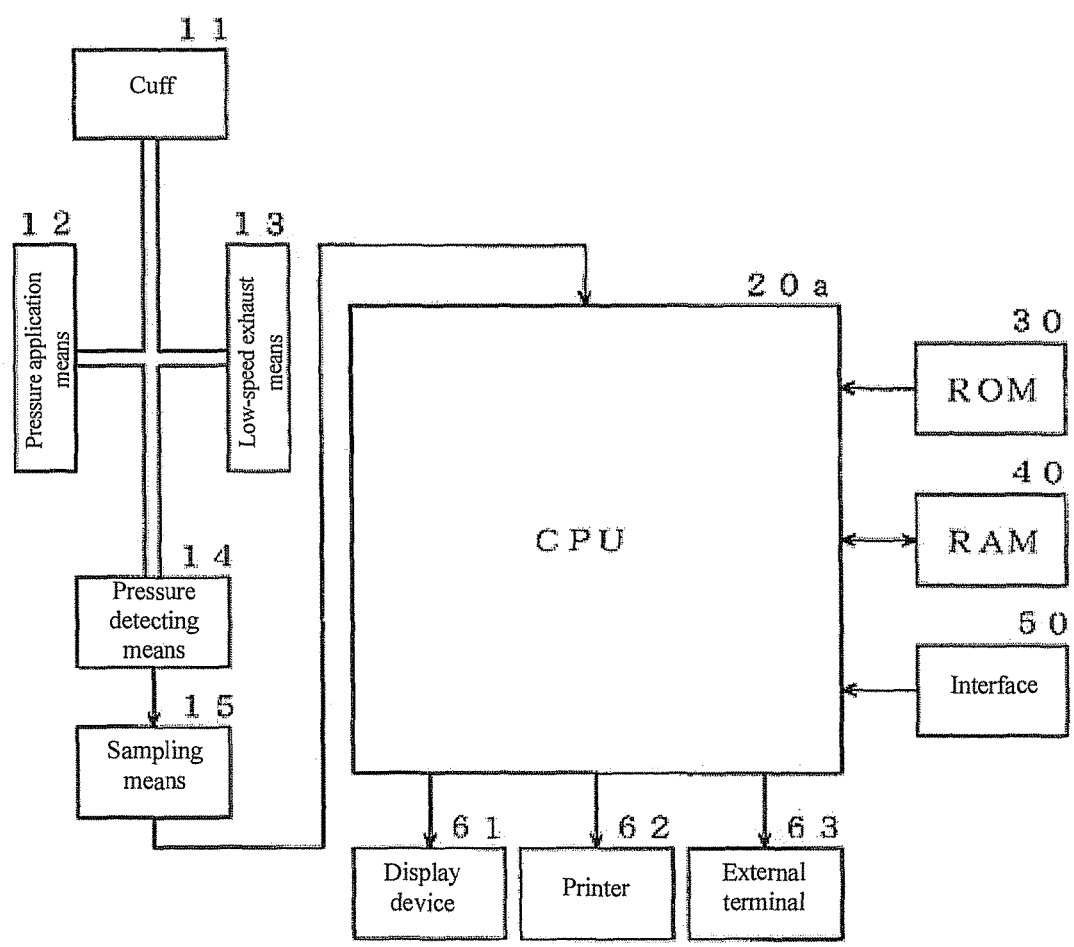
FIG. 10 is a block diagram of a vascular viscoelasticity evaluation device 200 according to Embodiment 2.

FIG. 10 is a block diagram of a vascular viscoelasticity evaluation device 200 in Embodiment 2 of the present invention.

The vascular viscoelasticity evaluation device 200 is an embodiment of detecting, in the vascular viscoelasticity evaluation device 100, the positive amplitude peak value Vf1 that occurs first and the negative amplitude peak value Vr2 that occurs second in a state in which a negative amplitude peak has been substantially reached.

More specifically, when the positive amplitude peak value Vf1 that occurs first and the negative amplitude peak value Vr2 that occurs second are detected, while in the vascular viscoelasticity evaluation device 100 they are detected in a state that an external force substantially the same as or greater than the systolic blood pressure has been exerted on the blood vessel, in the vascular viscoelasticity evaluation device 200, such values are detected in a state in which a negative amplitude peak has been substantially reached.

The vascular viscoelasticity evaluation device 200 is the same as the vascular viscoelasticity evaluation device 100, except that a CPU 20a is provided in place of the CPU 20.

Figure 11:
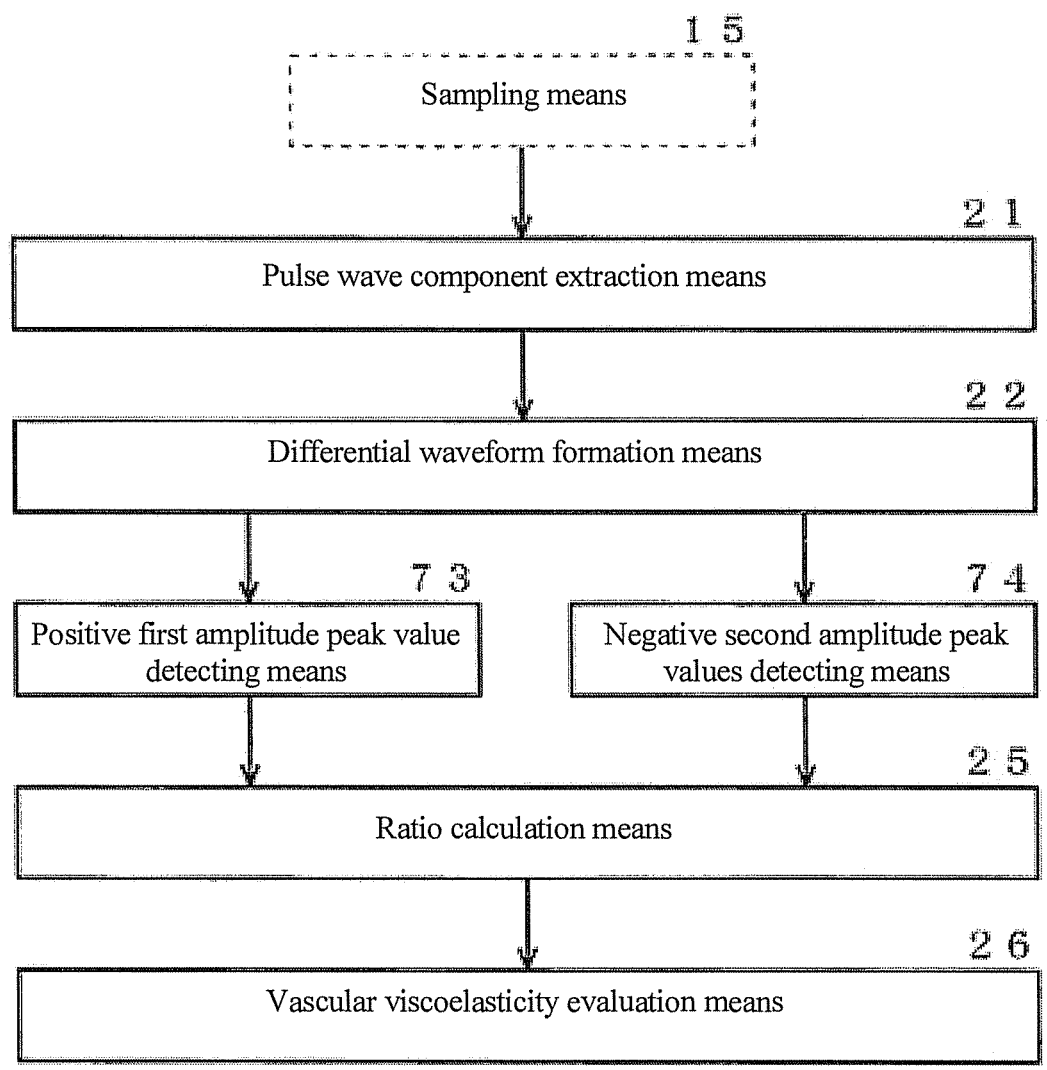
FIG. 11 is a diagram of the configuration of a CPU 20a in Embodiment 2.

FIG. 11 is a diagram illustrating the configuration of the CPU 20a of Embodiment 2.

In the CPU 20a, a positive first amplitude peak value detecting means 73 is provided in place of the positive first amplitude peak value detecting means 23 of CPU 20, and a negative second amplitude peak value detecting means 74 is provided in place of the negative second amplitude peak value detecting means 24 of CPU 20.

The positive first amplitude peak value detecting means 73 detects the positive amplitude peak value Vf1 that occurs first within one pulse wave of the differential waveform described above in a state in which a negative amplitude peak has been substantially reached.

The negative second amplitude peak value detecting means 74 detects the negative amplitude peak value Vr2 that occurs second within one pulse wave of the above-described differential waveform in a state in which the negative amplitude peak has been substantially reached. In other words, the negative second amplitude peak value detecting means 74 detects the negative amplitude peak value Vr2 that occurs second in the pulse wave in which the above-described positive amplitude peak value Vf1 that occurs first has been detected.

In Embodiment 2, reliability in the evaluation of vascular viscoelasticity is high when a pulse wave is measured with a single cuff and a determination index for vascular viscoelasticity is calculated on the basis of this measured pulse wave, and when the determination index for vascular viscoelasticity is calculated for a measurement subject that is a relatively young person.

Figure 12:
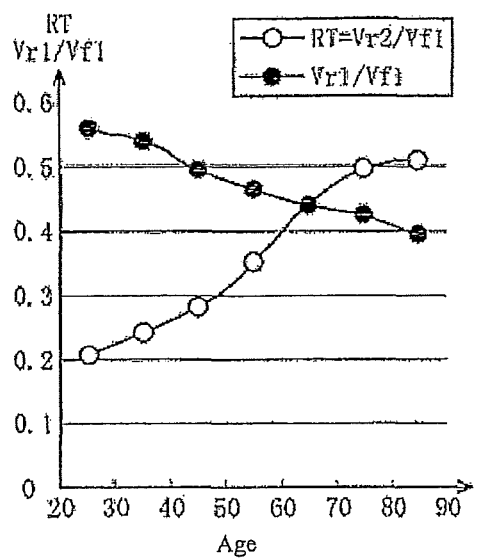
FIG. 12 is a graph illustrating characteristics of a ratio RT (Vr2/Vf1), Vr1/Vf1 with reference to age in Embodiment 2.

FIG. 12 a graph illustrating characteristics of the ratio RT (Vr2/Vf1), Vr1/Vf1 with reference to age in Embodiment 2.

It has been corroborated in a computer simulation performed by RIKEN that the above-described Vr2/Vr1 reflects the viscoelasticity of a central artery and is an index that is not greatly affected by the hardness of brachial blood vessels.

The vascular viscoelasticity evaluation means 26 evaluates vascular viscoelasticity on the basis of the ratio RT (Vr2/Vf1) calculated by the ratio calculation means 25. In this case, for example, average values for the ratio RT (Vr2/Vr1) with respect to age, sex, etc. are entered in a table in advance, and the risk of arteriosclerosis is determined by comparing these averages.

Figure 13:
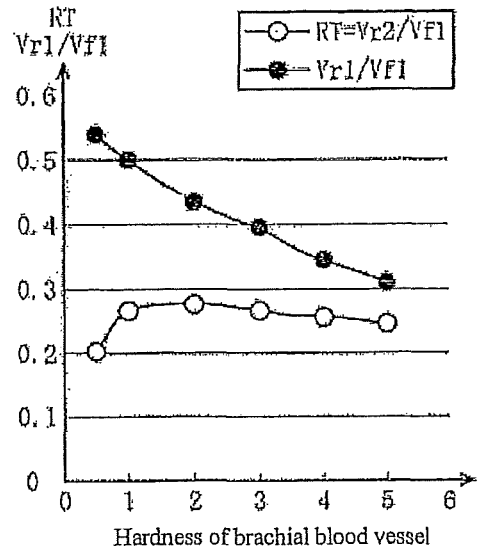
FIG. 13 is a graph illustrating characteristics of a ratio RT, Vr1/Vf1 of the hardness of brachial blood vessels at age 25 in Embodiment 2.

FIG. 13 is a graph illustrating characteristics of the ratio RT, Vr1/Vf1 of the hardness of brachial blood vessels at age 25.

Figure 14:
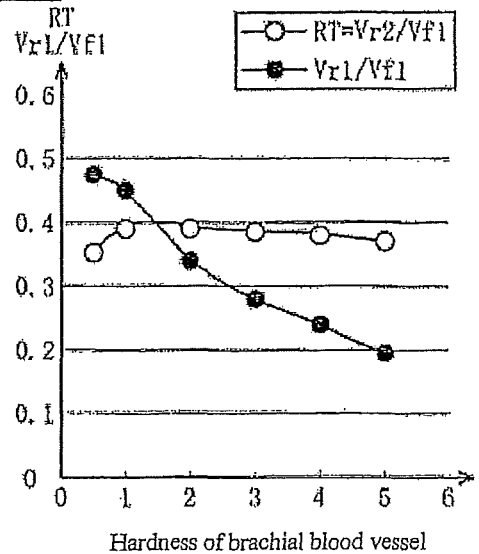
FIG. 14 is a graph illustrating characteristics of a ratio RT, Vr1/Vf1 of the hardness of brachial blood vessels at age 55 in Embodiment 2.

FIG. 14 is a graph illustrating characteristics of the ratio RT, Vr1/Vf1 of the hardness of brachial blood vessels at age 55.

Figure 15:
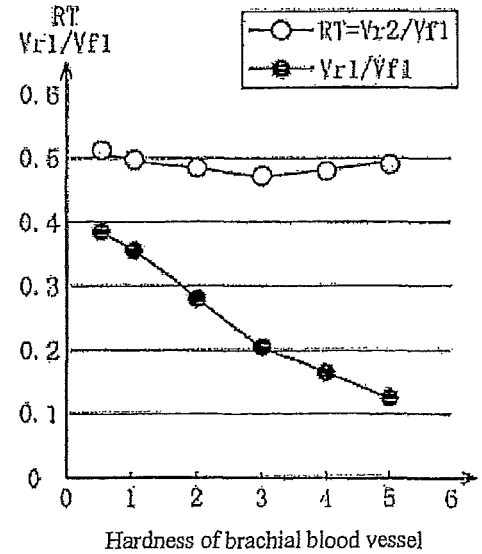
FIG. 15 is a graph illustrating characteristics of a ratio RT, Vr1/Vf1 of the hardness of brachial blood vessels at age 85.

FIG. 15 is a graph illustrating characteristics of the ratio RT, Vr1/Vf1 of the hardness of brachial blood vessels at age 85.

As seen from FIGS. 13 to 15, in a conventional method involving Vr1/Vf1 (the curve plotted with black circles), when there is a change in the hardness of brachial blood vessels, Vr1/Vf1 changes; in other words, Vr1/Vf1 is affected by the hardness of brachial blood vessels. However, in the ratio RT (Vr2/Vf1; the curve plotted with white circles), when the hardness of brachial blood vessels changes, there is almost no change in the ratio RT (Vr2/Vf1); in other words, the ratio RT (Vr2/Vf1) is able to evaluate the hardness of a central artery without being affected by the hardness of brachial blood vessels.

In the Embodiments described above, the cuff pressure is gradually reduced; however, the Embodiments is applicable also to a case in which the cuff pressure is gradually raised.

In addition, in the vascular viscoelasticity evaluation device 200, a difference can be used instead of using a ratio. In other words, it is possible that the positive amplitude peak value Vf1 that occurs first and the negative amplitude peak value Vr2 that occurs second are detected in a state in which a negative amplitude peak has been substantially reached, and then the vascular viscoelasticity is evaluated on the basis of the difference between the positive amplitude peak value Vf1 that occurs first and the negative amplitude peak value Vf2 that occurs second.

Embodiment 3

Figure 16:
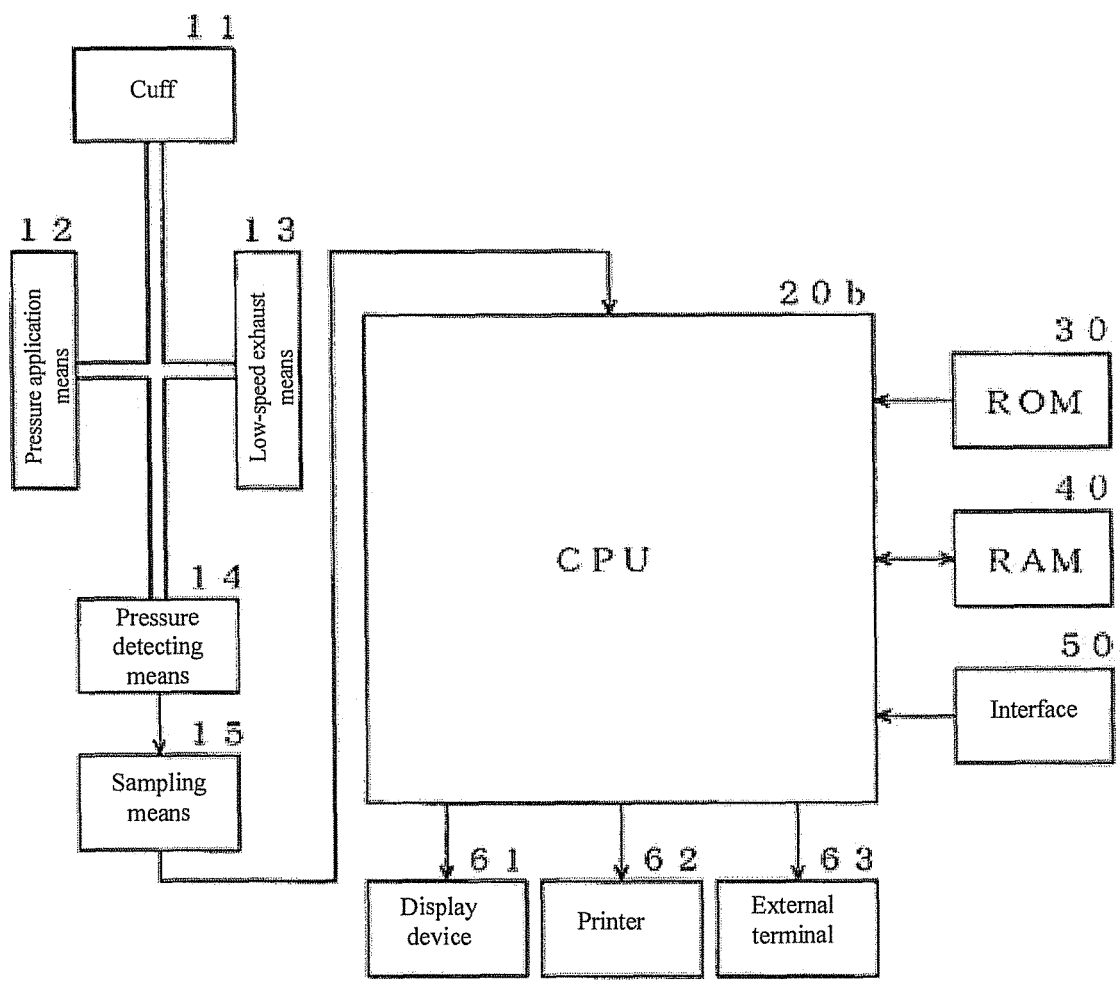
FIG. 16 is a block diagram of a vascular viscoelasticity evaluation device 300 in Embodiment 3.

FIG. 16 is a block diagram of a vascular viscoelasticity evaluation device 300 of Embodiment 3 of the present invention.

The vascular viscoelasticity evaluation device 300 is an embodiment in which, in the vascular viscoelasticity evaluation device 100, a pressure that is 40 mm Hg higher than the cuff pressure at the time of measurement of the systolic blood pressure is maintained for about 22 seconds, and the positive amplitude peak value Vf1 that occurs first and the negative amplitude peak value Vr2 that occurs second are detected within one pulse wave of a differential waveform obtained by the temporal differentiation of the pulse wave component extracted while this cuff pressure was being maintained.

The vascular viscoelasticity evaluation device 300 comprises the cuff 11, the pressure application means 12, the low-speed exhaust means 13, the pressure detecting means 14, the sampling means 15, a CPU 20b, the ROM 30, the RAM 40, the interface 50, the display device 61, the printer 62, and the external terminal 63.

Figure 17:
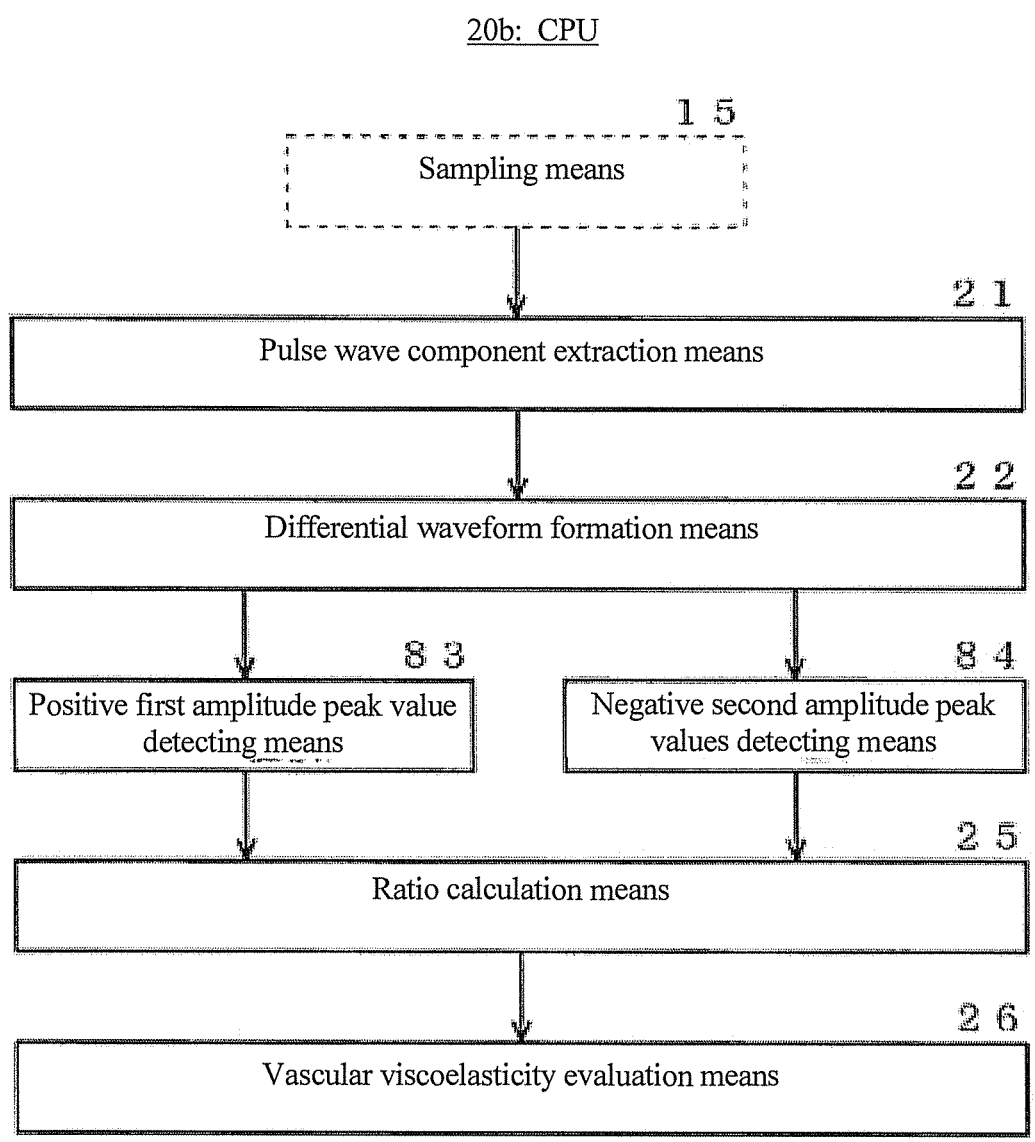
FIG. 17 is a block diagram of the function of a CPU 20b.

FIG. 17 is a block diagram showing the function of the CPU 20b.

Figure 18:
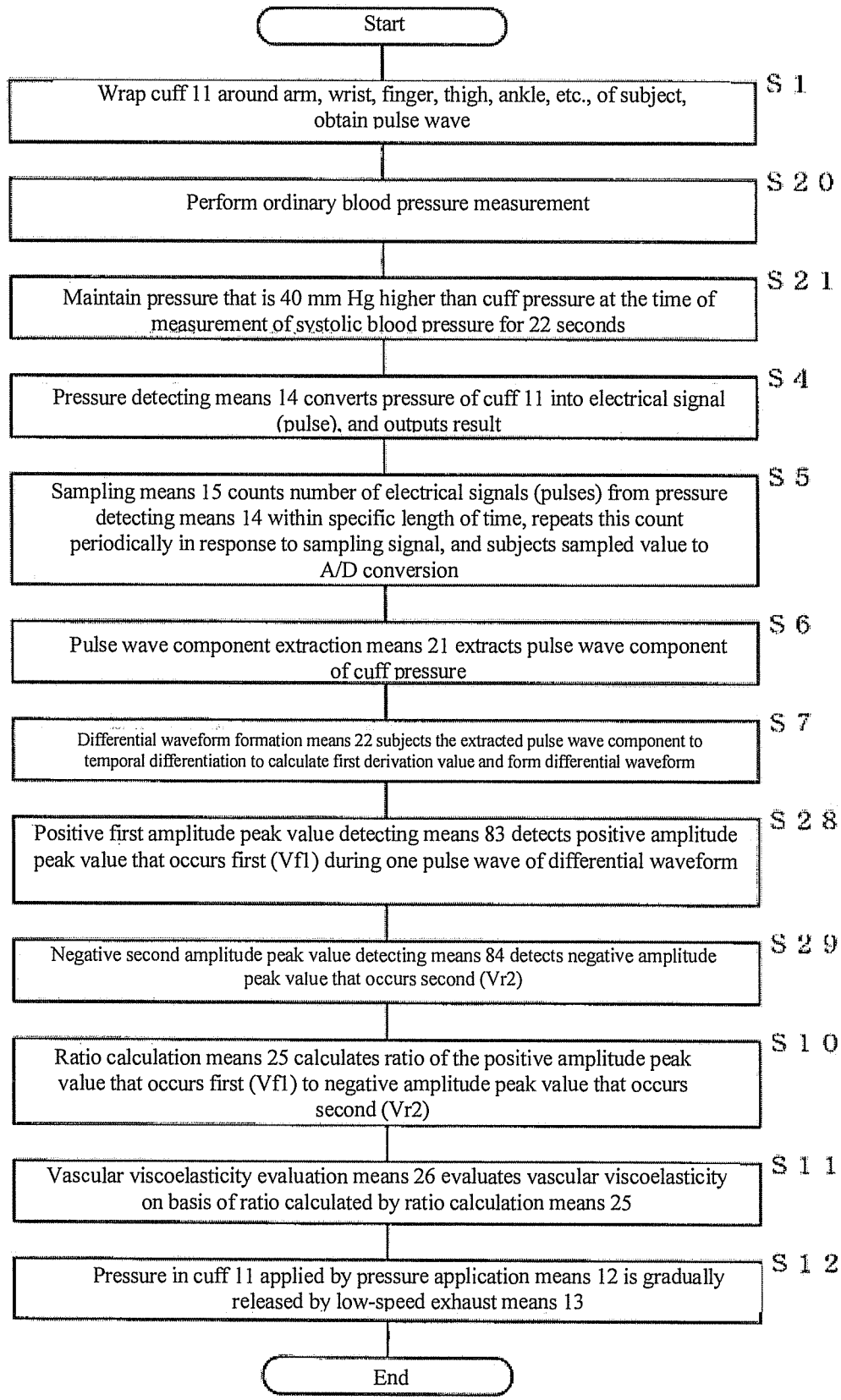
FIG. 18 is a flowchart of the operation in Embodiment 3.

The CPU 20b controls the entire vascular viscoelasticity evaluation device 300, and functionally, it works in conjunction with programs stored in the ROM 30 (FIG. 18 shows a corresponding flowchart) to form implementation of the pulse wave component extraction means 21, the differential waveform formation means 22, a positive first amplitude peak value detecting means 83, a negative second amplitude peak value detecting means 84, the ratio calculation means 25, and the vascular viscoelasticity evaluation means 26.

The pulse wave component extraction means 21 extracts the pulse wave component of the cuff pressure. The differential waveform formation means 22 subjects the pulse wave component extracted by the pulse wave component extraction means 21 to temporal differentiation to calculate a first derivation value and form a differential waveform.

The positive first amplitude peak value detecting means 83 maintains the pressure 40 mm Hg higher than the cuff pressure at the time of measurement of the systolic blood pressure for 22 seconds, and it detects the positive amplitude peak value Vf1 that occurs first within one pulse wave of a differential waveform obtained by the temporal differentiation of a pulse wave component extracted while the cuff pressure is being maintained.

The negative second amplitude peak value detecting means 84 detects the negative amplitude peak value Vr2 that occurs second in the pulse wave in which the positive amplitude peak value Vf1 that occurs first was detected. The ratio calculation means 25 calculates the ratio RT (Vr2/Vf1) of the positive amplitude peak value Vf1 that occurs first and the negative amplitude peak value Vf2 that occurs second. The vascular viscoelasticity evaluation means 26 evaluates vascular viscoelasticity on the basis of the ratio RT calculated by the ratio calculation means 25.

Next, the operation of Embodiment 3 will be described.

FIG. 18 is a flowchart of the operation in Embodiment 3.

First, in S1, the cuff 11 is wrapped around the arm, wrist, finger, thigh, ankle, etc., of a measurement subject to obtain a pulse wave. In S20, ordinary blood pressure measurement is performed to measure the systolic blood pressure. Then, in S21, a pressure that is 40 mm Hg higher than the cuff pressure at the time of measurement of the systolic blood pressure is maintained for 22 seconds, and in S4 the pressure detecting means 14 converts the pressure of the cuff 11 into an electrical signal (pulse) and outputs the result. In S5, the sampling means 15 counts the number of electrical signals (pulses) from the pressure detecting means 14 within a specific length of time, repeats this count periodically in response to a sampling signal and subjects the sampled value to A/D conversion.

In S6, the pulse wave component extraction means 21 extracts the pulse wave component of the cuff pressure. In S7, the differential waveform formation means 22 subjects the extracted pulse wave component to temporal differentiation to calculate a first derivation value and form a differential waveform.

In S28, the positive first amplitude peak value detecting means 83 detects the positive amplitude peak value Vf1 that occurs first within one pulse wave of the differential waveform described above. In S29, the negative second amplitude peak value detecting means 84 detects the negative amplitude peak value Vr2 that occurs second.

In S10, the ratio calculation means 25 calculates the ratio RT of the positive amplitude peak value Vf1 that occurs first to the negative amplitude peak value Vf2 that occurs second. In S11, the vascular viscoelasticity evaluation means 26 evaluates vascular viscoelasticity on the basis of the ratio RT calculated by the ratio calculation means 25. Then, in S12, the pressure inside the cuff 11 applied by the pressure application means 12 is gradually released by the low-speed exhaust means 13.

Figure 19:
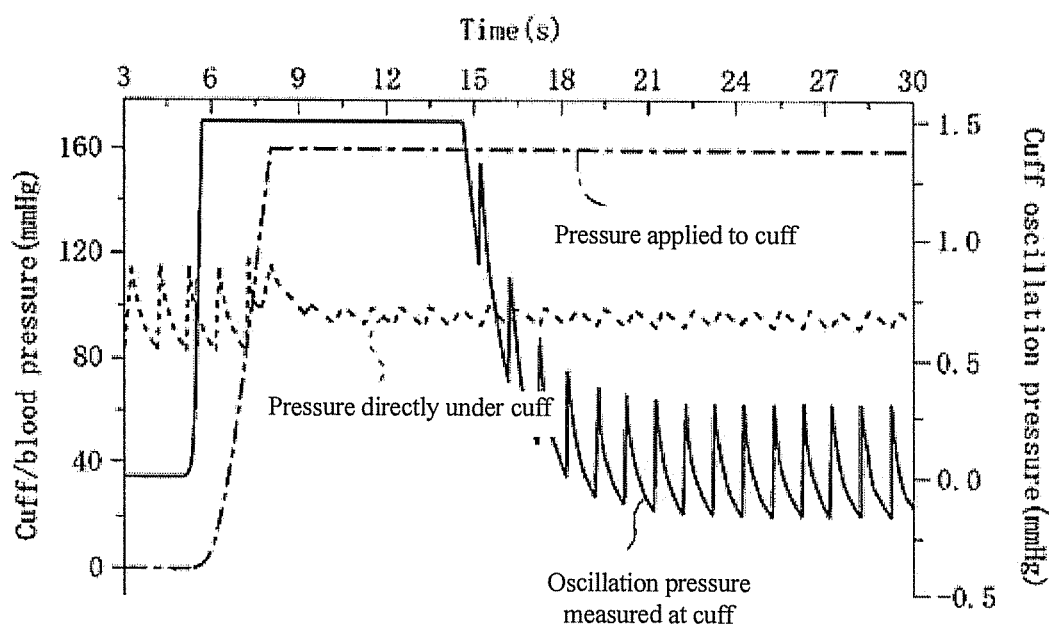
FIG. 19 is a graph of the relation between the pressure applied to the cuff and the cuff oscillation pressure measured at the cuff in Embodiment 3.

FIG. 19 is a graph of the relation between the pressure applied to the cuff and the cuff oscillation pressure measured at the cuff in Embodiment 3.

As seen from FIG. 19, the pressure applied to the cuff, which is indicated by a solid line (the oscillation pressure measured at the cuff), rises sharply to 160 mm Hg six (6) to eight (8) seconds after the start of measurement. This value of 160 mm Hg is a pressure obtained by adding 40 mm Hg to the systolic blood pressure. Once the cuff pressure reaches 160 mm Hg, it is maintained there for 22 seconds. Consequently, the transient pressure fluctuation component gradually disappears 14 seconds after the start of measurement, and the oscillation pressure measured at the cuff (the pressure indicated by the solid line) stabilizes in a state of equilibrium 20 seconds after the start of measurement. By way of maintaining this state for a specific length of time, it is possible that a plurality of pulse waves are extracted stably. Accordingly, it becomes easier to detect and eliminate body motion noise and the like that occur during measurement, and the peak value of a differential pulse wave can be detected more accurately.

In FIG. 19, the broken line indicates blood pressure directly under the cuff, and the one-dot chain line indicates the pressure applied to the cuff.

More specifically, in Embodiment 3, a pressure that is 40 mm Hg higher than the cuff pressure at the time of measurement of the systolic blood pressure is maintained for 22 seconds, and while maintaining the cuff pressure, the positive amplitude peak value that occurs first and the negative amplitude peak value that occurs second within one pulse wave of a differential waveform obtained by the temporal differentiation of an extracted pulse wave component are repeatedly detected while the cuff pressure is being maintained; accordingly, abnormal values can be detected and eliminated.

In addition, in the above Embodiment, a pressure that is 40 mm Hg higher than the cuff pressure at which the systolic blood pressure occurred is set, and this cuff pressure 160 mm Hg is maintained for 22 seconds. However, a pressure obtained by adding 30 to 50 mm Hg to the cuff pressure at which the systolic blood pressure occurred can be used instead as the cuff pressure. In other words, if measurement is performed by applying a pressure that is lower than 30 mm Hg to the cuff pressure at which the systolic blood pressure occurred, blood will start to flow to the blood vessel, and it will become difficult to eliminate body motion noise and the like that occur during measurement. On the other hand, if measurement is performed by applying a pressure that is higher than 50 mm Hg to the cuff pressure at which the systolic blood pressure occurred, the measurement subject may experience pain caused by this pressure. Therefore, it is preferable to set the cuff pressure to be a pressure obtained by adding 30 to 50 mm Hg to the cuff pressure at which the systolic blood pressure occurred.

Furthermore, the state in which the pressure is set higher than the systolic blood pressure may be maintained for some length of time other than 22 seconds, such as 5 to 30 seconds More specifically, if measurement is obtained while a state in which the pressure is set higher than the systolic blood pressure is sustained for a length of time shorter than 5 seconds, stability of the measured values is unable to obtain; and on the other hand, if measurement is obtained while the state in which the pressure is set higher than the systolic blood pressure is sustained for a length of time longer than 30 seconds, then blood congestion will occur, the characteristics of the blood vessel will change, and the reliability of the measured values will suffer. Accordingly, it is preferable that the state in which the pressure is set higher than the systolic blood pressure be sustained for a period of time between 5 and 30 seconds.

In other word, what should be done is to extract the above-described differential waveform obtained by the temporal differentiation of a pulse wave component while a cuff pressure that is higher by a specific amount than the cuff pressure at which the systolic blood pressure occurred is being maintained for a specific length of time by a cuff pressure maintenance means, and then to detect the positive amplitude peak value Vf1 that occurs first within one pulse wave of the above-described differential pulse wave obtained by the temporal differentiation of the extracted pulse wave component.

Furthermore, in the vascular viscoelasticity evaluation device 300, a difference can be used instead of using a ratio. In other words, the vascular viscoelasticity can be evaluated on the basis of the difference between the positive amplitude peak value Vf1 that occurs first and the negative amplitude peak value Vr2 that occurs second, which are both detected within one pulse wave of the above-described differential pulse wave obtained by the temporal differentiation of a pulse wave component extracted while a cuff pressure that is higher by a specific amount than the cuff pressure at which the systolic blood pressure occurred is being maintained for a specific length of time by the cuff pressure maintenance means.

In addition, if the various means described in the embodiments above are substituted for steps, then the above embodiments become examples of the vascular viscoelasticity evaluation method of the present invention.

Furthermore, in the above embodiments, hardware such as a circuit for implementing the functions of programs executed by a CPU can be provided instead of a CPU. Also, it is possible that part of the program is implemented with hardware, and the remaining portion is executed by a computer.

INDUSTRIAL APPLICABILITY

The present invention can be used in applications that require high reliability in the evaluation of arterial sclerosis when a pulse wave is measured with a single cuff and a determination index for arterial sclerosis is calculated on the basis of this measured pulse wave and when arterial sclerosis is evaluated for a measurement subject that is a relatively young person.

DESCRIPTION OF THE REFERENCE NUMERALS

100, 200, 300 Vascular viscoelasticity evaluation device
11 Cuff
20, 20a CPU
21 Pulse wave component extraction means
22 Differential waveform formation means
23, 73, 83 Positive first amplitude peak value detecting means
24, 74, 84 Negative second amplitude peak value detecting means
25 Ratio calculation means
26 Vascular viscoelasticity evaluation means

The invention claimed is:

1. A vascular viscoelasticity evaluation device, comprising:
   a cuff for generating a cuff pressure associated with a vascular viscoelasticity evaluation;
   a pressure detector for detecting the cuff pressure;
   a pulse wave component extraction means for extracting a pulse wave component of the cuff pressure detected by the pressure detector;
   a differential waveform formation means for subjecting the extracted pulse wave component to temporal differentiation to calculate a first derivation value and form a differential waveform;
   a positive first amplitude peak value $Vf_1$ detecting means for detecting a positive amplitude peak value $Vf_1$ that occurs first within one pulse wave of the differential waveform obtained by the temporal differentiation of the pulse wave component extracted in a state in which external force substantially the same as or greater than systolic blood pressure has been exerted on a blood vessel;
   a negative second amplitude peak value $Vf_2$ detecting means for detecting a negative amplitude peak value $Vf_2$ that occurs second in the pulse wave in which the positive amplitude peak value $Vf_1$ that occurs first was detected;
   a ratio calculation means for calculating a ratio $RT(Vf_2/Vf_1)$ of the positive amplitude peak value $Vf_1$ that occurs first to the negative amplitude peak value $Vf_2$ that occurs second as an evaluation index for evaluating vascular viscoelasticity, such that an influence of brachial blood vessel hardness on the evaluated vascular viscoelasticity is reduced; and
   an output device for presenting the evaluation index.

2. A vascular viscoelasticity evaluation device, comprising:
   a cuff for generating a cuff pressure associated with a vascular viscoelasticity evaluation;
   a pressure detector for detecting the cuff pressure;
   a pulse wave component extraction means for extracting a pulse wave component of the cuff pressure detected by the pressure detector;
   a differential waveform formation means for subjecting the extracted pulse wave component to temporal differentiation to calculate a first derivation value and form a differential waveform;
   a positive first amplitude peak value $Vf_1$ detecting means for detecting a positive amplitude peak value $Vf_1$ that occurs first within one pulse wave of the differential waveform obtained by the temporal differentiation of the pulse wave component extracted in a state in which external force substantially the same as or greater than systolic blood pressure has been exerted on a blood vessel;
   a negative second amplitude peak value $Vf_2$ detecting means for detecting a negative amplitude peak value $Vf_2$ that occurs second in the pulse wave in which the positive amplitude peak value $Vf_1$ that occurs first was detected;
   a difference calculation means for calculating a difference between the positive amplitude peak value $Vf_1$ that occurs first and the negative amplitude peak value $Vf_2$ that occurs second as an evaluation index for evaluating vascular viscoelasticity, such that an influence of brachial blood vessel hardness on the evaluated vascular viscoelasticity is reduced; and
   an output device for presenting the evaluation index.

3. A vascular viscoelasticity evaluation device, comprising:
   a cuff for generating a cuff pressure associated with a vascular viscoelasticity evaluation;
   a pressure detector for detecting the cuff pressure;
   a pulse wave component extraction means for extracting a pulse wave component of the cuff pressure detected by the pressure detector;
   a differential waveform formation means for subjecting the extracted pulse wave component to temporal differentiation to calculate a first derivation value and form a differential waveform;
   a positive first amplitude peak value $Vf_1$ detecting means for detecting a positive amplitude peak value $Vf_1$ that occurs first within one pulse wave of the differential waveform obtained by the temporal differentiation of the pulse wave component extracted in a state in which a negative amplitude peak has been substantially reached;
   a negative second amplitude peak value $Vf_2$ detecting means for detecting a negative amplitude peak value $Vf_2$ that occurs second in the pulse wave in which the positive amplitude peak value $Vf_1$ that occurs first was detected;
   a ratio calculation means for calculating a ratio $RT(Vf_2/Vf_1)$ of the positive amplitude peak value $Vf_1$ that occurs first to the negative amplitude peak value $Vf_2$ that occurs second as an evaluation index for evaluating vascular viscoelasticity, such that an influence of brachial blood vessel hardness on the evaluated vascular viscoelasticity is reduced; and
   an output device for presenting the evaluation index.

4. A vascular viscoelasticity evaluation device, comprising:
   a cuff for generating a cuff pressure associated with a vascular viscoelasticity evaluation;
   a pressure detector for detecting the cuff pressure;
   a pulse wave component extraction means for extracting a pulse wave component of the cuff pressure detected by the pressure detector;
   a differential waveform formation means for subjecting the extracted pulse wave component to temporal differentiation to calculate a first derivation value and form a differential waveform;
   a positive first amplitude peak value $Vf_1$ detecting means for detecting a positive amplitude peak value $Vf_1$ that occurs first within one pulse wave of the differential waveform obtained by the temporal differentiation of the pulse wave component extracted in a state in which a negative amplitude peak has been substantially reached;

a negative second amplitude peak value $Vf_2$ detecting means for detecting a negative amplitude peak value $Vf_2$ that occurs second in the pulse wave in which the positive amplitude peak value $Vf_1$ that occurs first was detected;

a difference calculation means for calculating a difference between the positive amplitude peak value $Vf_1$ that occurs first and the negative amplitude peak value $Vf_2$ that occurs second as an evaluation index for evaluating vascular viscoelasticity, such that an influence of brachial blood vessel hardness on the evaluated vascular viscoelasticity is reduced; and an output device for presenting the evaluation index.

5. A vascular viscoelasticity evaluation device, comprising:

a cuff for generating a cuff pressure associated with a vascular viscoelasticity evaluation;

a pressure detector for detecting the cuff pressure;

a pulse wave component extraction means for extracting a pulse wave component of the cuff pressure detected by the pressure detector;

a differential waveform formation means for subjecting the extracted pulse wave component to temporal differentiation to calculate a first derivation value and form a differential waveform;

a cuff pressure maintenance means for maintaining the cuff pressure for a specific length of time at a pressure that is higher by a specific amount than the cuff pressure at a time of measurement of a systolic blood pressure;

a positive first amplitude peak value $Vf_1$ detecting means for detecting a positive amplitude peak value $Vf_1$ that occurs first within one pulse wave of the differential waveform obtained by the temporal differentiation of the pulse wave component extracted while the cuff pressure maintenance means is maintaining the cuff pressure for the specific length of time;

a negative second amplitude peak value $Vf_2$ detecting means for detecting a negative amplitude peak value $Vf_2$ that occurs second in the pulse wave in which the positive amplitude peak value $Vf_1$ that occurs first was detected;

a ratio calculation means for calculating a ratio $RT(Vf_2/Vf_1)$ of the positive amplitude peak value $Vf_1$ that occurs first to the negative amplitude peak value $Vf_2$ that occurs second as an evaluation index for evaluating vascular viscoelasticity, such that an influence of brachial blood vessel hardness on the evaluated vascular viscoelasticity is reduced; and an output device for presenting the evaluation index.

6. The vascular viscoelasticity evaluation device according to claim 5, wherein the specific length of time is a time between 5 and 30 seconds.

7. A vascular viscoelasticity evaluation device, comprising:

a cuff for generating a cuff pressure associated with a vascular viscoelasticity evaluation;

a pressure detector for detecting the cuff pressure;

a pulse wave component extraction means for extracting a pulse wave component of the cuff pressure detected by the pressure detector;

a differential waveform formation means for subjecting the extracted pulse wave component to temporal differentiation to calculate a first derivation value and form a differential waveform;

a cuff pressure maintenance means for maintaining the cuff pressure for a specific length of time at a pressure that is higher by a specific amount than the cuff pressure at a time of measurement of a systolic blood pressure;

a positive first amplitude peak value $Vf_1$ detecting means for detecting a positive amplitude peak value $Vf_1$ that occurs first within one pulse wave of the differential waveform obtained by the temporal differentiation of the pulse wave component extracted while the cuff pressure maintenance means is maintaining the cuff pressure for the specific length of time;

a negative second amplitude peak value $Vf_2$ detecting means for detecting a negative amplitude peak value $Vf_2$ that occurs second in the pulse wave in which the positive amplitude peak value $Vf_1$ that occurs first was detected;

a difference calculation means for calculating a difference between the positive amplitude peak value $Vf_1$ that occurs first and the negative amplitude peak value $Vf_2$ that occurs second as an evaluation index for evaluating vascular viscoelasticity, such that an influence of brachial blood vessel hardness on the evaluated vascular viscoelasticity is reduced; and an output device for presenting the evaluation index.

8. The vascular viscoelasticity evaluation device according to claim 7, wherein the specific length of time is a time between 5 and 30 seconds.

9. A program for making a computer function as a means for constituting the vascular viscoelasticity evaluation device according to claim 8.

10. A program for making a computer function as a means for constituting the vascular viscoelasticity evaluation device according to any one of claims 1 to 6.

11. A vascular viscoelasticity evaluation method, comprising:

a cuff pressure generation step in which a cuff generates a cuff pressure associated with a vascular viscoelasticity evaluation;

a pressure detection step in which a pressure detector detects the cuff pressure;

a pulse wave component extraction step in which a pulse wave component extraction means extracts a pulse wave component of the cuff pressure detected by the pressure detector;

a differential waveform formation step in which a differential waveform formation means subjects the extracted pulse wave component to temporal differentiation to calculate a first derivation value and form a differential waveform;

a positive first amplitude peak value $Vf_1$ detecting step in which a positive first amplitude peak value $Vf_1$ detecting means detects a positive amplitude peak value $Vf_1$ that occurs first within one pulse wave of the differential waveform obtained by the temporal differentiation of the pulse wave component extracted in a state in which external force substantially the same as or greater than a systolic blood pressure has been exerted on a blood vessel;

a negative second amplitude peak value $Vf_2$ detecting step in which a negative second amplitude peak value $Vf_2$ detecting means detects a negative amplitude peak value $Vf_2$ that occurs second in the pulse wave in which the positive amplitude peak value $Vf_1$ that occurs first was detected;

a calculation step in which a calculation means calculates a ratio $RT(Vf_2/Vf_1)$ of the positive amplitude peak value $Vf_1$ that occurs first to the negative amplitude peak value $Vf_2$ that occurs second as an evaluation index for evaluating vascular viscoelasticity, or calculates a difference between the positive amplitude peak value $Vf_1$ that occurs first and the negative amplitude peak value $Vf_2$ that occurs second as the evaluation index for evaluating the vascular viscoelasticity, wherein the calculation step determines the evaluation index such that an influence of brachial blood vessel hardness on the evaluated vascular viscoelasticity is reduced; and a presentation step in which an output device presents the evaluation index.

12. A vascular viscoelasticity evaluation method, comprising:

a cuff pressure generation step in which a cuff generates a cuff pressure associated with a vascular viscoelasticity evaluation;

a pressure detection step in which a pressure detector detects the cuff pressure;

a pulse wave component extraction step in which a pulse wave component extraction means extracts a pulse wave component of the cuff pressure detected by the pressure detector;

a differential waveform formation step in which a differential waveform formation means subjects the extracted pulse wave component to temporal differentiation to calculate a first derivation value and form a differential waveform;

a positive first amplitude peak value $Vf_1$ detecting step in which a positive first amplitude peak value $Vf_1$ detecting means detects a positive amplitude peak value $Vf_1$ that occurs first within one pulse wave of the differential waveform obtained by the temporal differentiation of the pulse wave component extracted in a state in which a negative amplitude peak has been substantially reached;

a negative second amplitude peak value $Vf_2$ detecting step in which a negative second amplitude peak value $Vf_2$ detecting means detects a negative amplitude peak value $Vf_2$ that occurs second in the pulse wave in which the positive amplitude peak value $Vf_1$ that occurs first was detected;

a calculation step in which a calculation means calculates a ratio of the positive amplitude peak value $Vf_1$ that occurs first to the negative amplitude peak value $Vf_2$ that occurs second as an evaluation index for evaluating vascular viscoelasticity, or calculates a difference between the positive amplitude peak value $Vf_1$ that occurs first and the negative amplitude peak value $Vf_2$ that occurs second as the evaluation index for evaluating the vascular viscoelasticity, wherein the calculation step determines the evaluation index such that an influence of brachial blood vessel hardness on the evaluated vascular viscoelasticity is reduced; and a presentation step in which an output device presents the evaluation index.

13. A vascular viscoelasticity evaluation method, comprising:

a cuff pressure generation step in which a cuff generates a cuff pressure associated with a vascular viscoelasticity evaluation;

a pressure detection step in which a pressure detector detects the cuff pressure;

a pulse wave component extraction step in which a pulse wave component extraction means extracts a pulse wave component of the cuff pressure detected by the pressure detector;

a differential waveform formation step in which a differential waveform formation means subjects the extracted pulse wave component to temporal differentiation to calculate a first derivation value and form a differential waveform;

a cuff pressure maintenance step in which a cuff pressure maintenance means maintains the cuff pressure for a specific length of time at a pressure that is higher by a specific amount than the cuff pressure at a time of measurement of a systolic blood pressure;

a positive first amplitude peak value $Vf_1$ detecting step in which a positive first amplitude peak value $Vf_1$ detecting means detects a positive amplitude peak value $Vf_1$ that occurs first within one pulse wave of the differential waveform obtained by the temporal differentiation of the pulse wave component extracted while the cuff pressure maintenance means is maintaining the cuff pressure for the specific length of time;

a negative second amplitude peak value $Vf_2$ detecting step in which a negative second amplitude peak value $Vf_2$ detecting means detects a negative amplitude peak value $Vf_2$ that occurs second in the pulse wave in which the positive amplitude peak value $Vf_1$ that occurs first was detected;

a calculation step in which a calculation means calculates a ratio of the positive amplitude peak value $Vf_1$ that occurs first to the negative amplitude peak value $Vf_2$ that occurs second as an evaluation index for evaluating vascular viscoelasticity, or calculates a difference between the positive amplitude peak value $Vf_1$ that occurs first and the negative amplitude peak value $Vf_2$ that occurs second as the evaluation index for evaluating the vascular viscoelasticity, wherein the calculation step determines the evaluation index such that an influence of brachial blood vessel hardness on the evaluated vascular viscoelasticity is reduced; and a presentation step in which an output device presents the evaluation index.

* * * * *